US008287911B2

(12) United States Patent
Terato et al.

(10) Patent No.: US 8,287,911 B2
(45) Date of Patent: *Oct. 16, 2012

(54) ENDOTOXIN ADSORBENT FOR THE PREVENTION AND TREATMENT OF AUTOIMMUNE DISEASES

(75) Inventors: Kuniaki Terato, Redmonde, WA (US); Hiroshi Shionoya, Saitama (JP); Sadaichi Iwashita, Fukuoka (JP)

(73) Assignees: Chondrex Inc., Redmonde, WA (US); Hiroshi Shinoya, Tokorozawa-shi, Saitama (JP); Muromachi Chemical Co., Ltd., Ohmuta-shi, Fukuoka (JP)

(*) Notice: Subject to any disclaimer, the term of this patent is extended or adjusted under 35 U.S.C. 154(b) by 132 days.

This patent is subject to a terminal disclaimer.

(21) Appl. No.: 12/804,945

(22) Filed: Aug. 2, 2010

(65) Prior Publication Data

US 2010/0303923 A1  Dec. 2, 2010

Related U.S. Application Data

(62) Division of application No. 11/518,393, filed on Sep. 7, 2006, now Pat. No. 7,799,347.

(51) Int. Cl.
  *B29C 35/00* (2006.01)
  *B29C 65/00* (2006.01)
  *A01J 21/00* (2006.01)
  *A01J 25/12* (2006.01)
  *E04F 13/08* (2006.01)

(52) U.S. Cl. .................. 424/501; 424/404
(58) Field of Classification Search .......... None
See application file for complete search history.

(56) References Cited

U.S. PATENT DOCUMENTS

| | | | |
|---|---|---|---|
| 4,510,128 A | 4/1985 | Khanna | |
| 6,090,292 A * | 7/2000 | Zimmermann et al. | 210/690 |
| 7,799,347 B2 * | 9/2010 | Terato et al. | 424/501 |
| 2002/0130082 A1 | 9/2002 | Todokoro et al. | |
| 2007/0207187 A1 | 9/2007 | Yajima et al. | |
| 2008/0063645 A1 * | 3/2008 | Terato et al. | 424/140.1 |

FOREIGN PATENT DOCUMENTS

| | | |
|---|---|---|
| EP | 0 955 312 A2 | 11/1999 |
| JP | 58-013519 | 1/1983 |
| JP | 08-026954 | 1/1996 |
| JP | 11-335396 | 12/1999 |
| JP | 2002-263486 | 9/2002 |
| JP | 2002-311029 | 10/2002 |
| JP | 2004-292357 | 10/2004 |
| JP | 2006-151914 | 6/2006 |
| WO | WO 87/07531 | 12/1987 |
| WO | WO 99/06440 | 2/1999 |
| WO | WO 2006/035979 A1 | 4/2006 |

OTHER PUBLICATIONS

"Commensal bacteria (normal microflora), mucosal immunity and chronic inflammatory and autoimmune diseases" by H. Tlaskalova-Hogenova et al, *Immunology Letters*, vol. 93, (2004), pp. 97-108.
"Reactivation of Antigen-Induced Arthritis in Mice by Oral Administration of Lipopolysaccharide" by S. Yoshino et al, *Scandinavian Journal of Immunology*, vol. 62, (2005), pp. 117-122.
"Endotoxic Activity in Faeces of Mice from Different Microbiological Environments" by S. Kawamura et al, *Research in Microbiology*, vol. 141, (1990), pp. 1095-1101.
"Effects of *Porphyromonas gingivalis* on Cell Cycle Progression and Apoptosis of Primary Human Chrondrocytes" by N. Pischon et al, *Ann Rheum. Dis.*, (2008), doi:10.1136/ard.2008.102392, pp. 1-16.
"*Porphyromonas gingivalis* May Play an Important Role in the Pathogenesis of Periodontitis-Associated Rheumatoid Arthritis" by F. Liao et al, *Medical Hypothesis Journal*, vol. 72, (2009), pp. 732-735.
"Immunologic Self-Tolerance Maintained by Activated T Cells Expressing IL-2 Receptor α-Chains (CD25)" by S. Sakaguchi et al, *Journal of Immunology*, vol. 155, (1995) pp. 1151-1164.
"Gut Microbiota and Lipopolysaccharide Content of the Diet Influence Development of Regulatory T Cells: Studies in Germ-Free Mice" by T. Hrncir et al, *BMC Immunology*, vol. 9, (2008), doi:10.1186/1471-2172-9-65, pp. 1-11.
"Influences of Microbiota on Intestinal Immune System Development" by J. Cebra, *Am J Clin. Nutr*, vol. 69, (1999), pp. 1046S-1051S.
"Mucosal Immunity: Its Role in Detense and Allergy" by H. Tlaskalova-Hogenova et al, *Int Arch Allergy Immunol*, vol. 128, (2002), pp. 77-89.
Commensal Bacterial (Normal Microflora) Mucosal Immunity and Chronic Inflammatory and Autoimmune Diseases, by H. Tlaskalova-Hogenova et al, *Immunol Lett*, (2004) 93(2-3): 97-108 (AbstractPlus—one page).
Oral Administration of Lipopolysaccharides Activates B-1 Cells in the Peritoneal Cavity and Lamina Propria of the Gut and Induces Autoimmune Symptoms in an Autoantibody Transgenic Mouse, by M. Murakami et al, *J. Exp. Med.*, vol. 180 (1994) pp. 111-121.

(Continued)

*Primary Examiner* — Amy Juedes
(74) *Attorney, Agent, or Firm* — Flynn, Thiel, Boutell & Tanis, P.C.

(57) ABSTRACT

It is believed that the abnormal absorption of endotoxin present in the gastrointestinal tract relates to the pathogenesis of autoimmune diseases such as rheumatoid arthritis. In an animal model for rheumatoid arthritis, it is observed that arthritis is improved by removing endotoxin. The present invention provides an endotoxin-adsorbent, which is capable of removing endotoxin in the gastrointestinal tract and can be administered to humans safely. By using a non-digestible and non-absorbable, and therefore, safe endotoxin-adsorbent, which has a high endotoxin-binding capacity for removing large amounts of endotoxin present in the gastrointestinal tract, it is possible to prevent and treat autoimmune diseases such as rheumatoid arthritis.

4 Claims, No Drawings

OTHER PUBLICATIONS

"Effects of Breeding Environments on Generation and Activation of Autoreactive B-1 Cells in Anti-red Blood Cell Autoantibody Transgenic Mice" by M. Murakami et al, *J. Exp. Med.*, vol. 185, No. 4, (1997), pp. 791-794.
"Oral Administration of Lipopolysaccharide Exacerbates Collagen-Induced Arthritis in Mice" by S. Yoshino et al, *Journal of Immunology*, (1999), pp. 3417-3422.
"Reactivation of Antigen-Induced Arthritis in Mice by Oral Administration of Lipopolysaccharide" by S. Yoshino et al, *Scand J Immunol*, (2005), 62(2):117-22 (Abstract Plus—one page).
"The Mechanism of Autoantibody Formation to Cartilage in Rheumatoid Arthritis: Possible Cross-Reaction of Antibodies to Dietary Collagens with Autologous Type II Collagen" by K. Terato et al, *Clinical Immunology and Immunopathology*, vol. 79, No. 2, (1996), pp. 142-154.
"Collagen-Induced Arthritis in Mice: Synergistic Effect of *E. coli* Lipopolysacharide Bypasses Epitope Specificity in the Induction of Arthritis with Monoclonal Antibodies to Type II Collagen" by K. Terato et al, *Autoimmunity*, vol. 22, (1995), pp. 137-147.
"Endotoxic Activity in Faeces of Mice from Different Microbiological Environments" by S. Kawamura et al, *Res. Microbiol* (1990) 141(9):1095-101 (AbstractPlus—one page).
"*Porphyromonas gingivalis* May Play an Important Role in the Pathogenesis of Periodontitis-Associated Rheumatoid Arthritis" by F. Liao et al, *Med Hypotheses*, (2009), 72(6):732-5 (AbstractPlus—one page).
"Induction of Chronic Autoimmune Arthritis in DBA/1 Mice by Oral Administration of Type II Collagen and *Escherichia coli* Lipopolysaccharide" by K. Terato et al, *British Journal of Rheumatology*, vol. 35, (1996), pp. 828-838.
"Effects of *Porphyromonas gingivalis* on Cell Cycle Progression and Apoptosis of Primary Human Chondrocytes" by N. Pischon et al, *Ann Rheum Dis*, (2008), (AbstractPlus—one page).
Microbiology, by B.D. Davis, et al, *Harper International Edition*, 1970, pp. 615-617.
Induction of Chromic Autoimmune Arthritis in DBA/1 Mice by Oral Administration of Type II Collagen and *Escherichia coli* Lipopolysaccharide, by K. Terato et al, *British Journal of Rheumatlogy*, 1996, vol. 35, pp. 828-838.
Collagen-Induced Arthritis in Mice: Synergistic Effect of *E. coli* Lipopolysaccharide Bypasses Epitope Specificity in the Induction of Arthritis with Monoclonal Antibodies to Type II Collagen, by K. Terato et al, *Autoimmunity*, 1995, vol. 22, pp. 137-147.
Lipopolysaccharide Injection Induces Relapses of Experimental Autoimmune Encephalomyelitis in Nontransgenic Mice via Bystander Activation of Autoreactive CD4+Cells, by A. Nogai et al, *Journal of Immunology*, 2005, vol. 175, pp. 959-966.
Endotoxin Induces Late Increase in the Production of Pulmonary Proinflammatory Cytokines in a Murine Lupus-Like Pristane-Primed Model, by B.S. Chae et al, *Arch. Pharm. Res.*, 2006, vol. 29, pp. 302-309.
LPS and Freund's Adjuvant Initiate Different Inflammatory Circuits in Experimental Autoimmune Thyroiditis, by D. Damotte et al, *Eur. Cytokine Netw.*, Mar. 2003, vol. 14, pp. 52-59.
Immune Response to Lipopolysaccharide in Primary Biliary Cirrhosis and Autoimmune Diseases, by E. Ballot et al, *Journal of Autoimmunity*, 2004, vol. 22, pp. 153-158.
Carbohydrate Mimicry between Human Ganglioside GM1 and *Campylobacter jejuni* Lipooligosaccharide causes Guillain-Barré Syndrome, by N. Yuki et al, *Proc. Nat'l Aca. Sci. USA*, 2004, vol. 101, pp. 11404-11409.
Detection of Cellulolytic Bacteria from the Human Colon, by J. Kopecny et al, *Folia Microbiol.*, 2004, vol. 49, pp. 175-177.
Dietary-fiber-degrading Enzymes from a Human Intestinal *Clostridium* and their Application to Oligosaccharide Production from Nonstarchy Polysaccharides using Immobilized Cells, by N. Nakajima et al, *Appl. Microbiol. Biotechnol.*, 2002, vol. 59, pp. 182-189.
Induction of Arthritis with Monoclonal Antibodies to Collagen, by K. Terato et al, *Journal of Immunology*, 1992, vol. 148, pp. 2103-2108.
M Cells in Peyer's Patches of the Intestine, by A. Gebert et al, *International Review of Cytology*, 1996, vol. 167, pp. 91-159.
How do you diagnose rheumatoid arthritis early?, by M. Quinn et al, Best Practice & Research Clinical Rheumatology, vol. 15, No. 1, 2001, pp. 49-66.
Sigma-Aldrich Particle Size Conversion Table, 2 pgs, 1999.
Size effect on systemic and mucosal immune responses induced by oral administration of biodegradable microspheres, by Y. Tabata et al, *Vaccine*, vol. 14., No. 17/18, 1996, pp. 1677-1685.
Endotoxin Binding by Charged and Uncharged Resins, by J. Nolan et al, Proceedings of the Society for Experimental Biology and Medicine, vol. 149, 1975, pp. 766-770.
Gut Endotoxin Restriction Prevents Catabolic Changes in Glutamine Metabolism After Surgery in the Bile Duct-Ligated Rat, by A. Houdijk, M.D., et al, Annals of Surgery, vol. 225, No. 4, 1997, pp. 391-400.
Bovine immunoglobulin concentrate-*Clostridium difficile* retains C *difficile* toxin neutralising activity after passage through the human stomach and small intestine, by M. Warny et al, *Gut*, vol. 44, 1999, pp. 212-217.
Susceptibility to Adjuvant-Induced Arthritis Among Germfree, Specific-Pathogen-Free, and Conventional Rats, by O. Kohashi et al, Infection and Immunity, vol. 26, No. 3, Dec. 1979, pp. 791-794.
Lipopolysaccharide-Activated B Cells Down-Regulate Th1 Immunity and Prevent Autoimmune Diabetes in Nonobese Diabetic Mice, by J. Tian et al, *Journal of Immunology*, vol. 167, 2001, pp. 1081-1089.
Role ot the Bowel Flora for Development of Immunity to hsp 65 and Arthritis in Three Experimental Models, by J. Björk et al, *Scand. J. Immunol.*, vol. 40, 1994, pp. 648-652.

\* cited by examiner

ENDOTOXIN ADSORBENT FOR THE PREVENTION AND TREATMENT OF AUTOIMMUNE DISEASES

CROSS-REFERENCE TO RELATED APPLICATIONS

This application is a divisional of prior U.S. application Ser. No. 11/518,393, filed Sep. 7, 2006 now U.S. Pat. No. 7,799,347.

FIELD OF THE INVENTION

This invention relates to an endotoxin-adsorbent for preventing and treating autoimmune diseases, such as rheumatoid arthritis, by removing endotoxin in the gastrointestinal tract.

RELATED ARTS

Lipopolysaccharide (LPS), a component of the outer cell membrane of gram-negative bacteria, is known as endotoxin; and the lipid A component is the fatal toxic domain of LPS (Microbiology. David B D, Dulbecco R, Eisen E N, Harold S, Ginsberg H S, Barry W A. Harper International Edition 615-617, 1970).

Endotoxin has a variety of physiological and pathological effects and causes endotoxin shock in animals within one hour if enough amounts of LPS were injected. Since it causes fever even at low dose, it is also known as a pyrogen. Therefore, the contamination of endotoxin in medical products such as injection products used as a non-oral administration is strictly prevented.

Since large numbers of a variety of gram-negative microorganisms, such as *E. coli*, invariably reside in the gastrointestinal tract of animals and humans, a large amount of endotoxin consistently is present in the gastrointestinal tract. However, animals and humans do not suffer a fever in general, indicating that endotoxin is barely absorbed from intestinal walls due to its large molecular size or due to mucosal immune barrier systems such as the IgA antibody barrier on intestinal walls.

The immune system is one of the major self-defense systems for a host to keep homeostasis by recognizing and preventing the invasion of foreign substances such as microorganisms as well as the growth of abnormal cells such as cancer cells, and by excluding them from the body. However, once this system is destroyed for unknown reasons, the immune system starts to attack self-components, and as a consequence, induces a variety of intractable diseases, so called "autoimmune diseases". The following diseases are known as autoimmune diseases: rheumatoid arthritis, autoimmune hepatitis, autoimmune nephritis, autoimmune labyrinthitis, autoimmune encephalomyelitis, autoimmune chronic thyroiditis, type I diabetes, systemic lupus erythematosus, polydermatomyositis, psoriasis, Sjorgren syndrome, ulcerative colitis, Crohn's disease, and Guillain-Barre syndrome.

Rheumatoid arthritis is an example of a typical autoimmune disease. Since large numbers of patients suffer this painful disease and their quality of life in society is interfered with by their limited function, this disease has been given a lot of social attention. The majority of patients with rheumatoid arthritis are forced to be confined to bed rest as the progress of arthritis, such as articular destruction, joint deformity, mobility impairment and pain increases. Currently, autoimmune diseases are treated with non-steroidal anti-inflammatory drugs, anti-inflammatory steroids, immune suppressants, and anti-cytokine antibodies such as Remicade. These therapeutic agents only suppress abnormal immune systems and inflammatory reactions, and are used to target specific symptoms, but not intended to cure the disease. Although several hypotheses for the causes of rheumatoid arthritis have been proposed, the etiology and the pathology of this disease remain unknown.

Based on the analysis of auto-antibodies in sera and cartilages from patients with rheumatoid arthritis, we have reached a hypothesis that the chronic abnormal absorption of mimic antigens and bacterial toxins from the gastrointestinal tract due to increased mucosal permeability is the fundamental, common disorder of autoimmune diseases. This hypothesis was proved by the following arthritis models in experimental animals. We administered purified heterologous type II collagen with and without the use of LPS to mice by the oral route, and successfully induced three types of chronic arthritis in mice. Most importantly, bacterial toxins, such as endotoxin, are not only capable of disturbing immune homeostasis by stimulating host immune systems non-specifically, but also capable of inducing inflammatory diseases such as arthritis. Based on these observations, the inventors of this invention focused on the pathogenic roles of LPS, which is a dominant bacterial toxin produced by intestinal flora in large quantities, and reached a hypothesis that autoimmune diseases could be prevented and treated by blocking the absorption of excess amounts of LPS from the gastrointestinal tract by using an endotoxin-adsorbent.

To begin, mice were administered chick type II collagen by the oral route for more than 10 weeks. Mice developed antibodies to chick type II collagen, which cross-reacts to autologous type II collagen, and as a consequence, mice developed clinically apparent arthritis (Terato K, Ye X Y, Miyahara H, Cremer M A, and Grifiths M M. Induction of auto-immune arthritis in DBA/1 mice by oral administration of type II collagen. Br. J. Rheum. 35:828-838, 1996).

Since autoantibodies to cartilage are not always capable of inducing arthritis in experimental animals and humans, it was assumed that a secondary factor(s) is involved in the induction of arthritis in patients with rheumatoid arthritis. Although a variety of bacterial toxins are considered as a potential secondary pathogenic factor, it is most likely that endotoxin will play the dominant pathological role in the majority of patients with autoimmune diseases, because endotoxin is the most widely and commonly existing at high levels in the gastrointestinal tract. In order to test this possibility, mice were injected with a non-arthritogenic dose of monoclonal anti-type II collagen antibody cocktail and then received LPS by IP and oral route. The control mice receiving anti-type II collagen antibody alone did not develop arthritis, whereas, both groups of mice receiving LPS by IP and by oral administration developed severe arthritis, indicating that environmental factors such as LPS play important pathological roles in autoimmune diseases (Terato K, Harper D S, Griffiths M M, Hasty I D A, Ye X Y, Cremer M A and Seyer J S. Collagen-induced arthritis: Synergistic effect of *E. coli* lipopolysaccharide bypass epitope specificity in the induction of arthritis with monoclonal antibodies to type II collagen. Autoimmunity 22:137-147, 1995).

It has been known that endotoxin is not only involved in rheumatoid arthritis but also involved in a variety of autoimmune diseases such as autoimmune encephalomyelitis (Nagai A et al. J. Immunol. 175:959-966, 2005), lupus lung injury (Chae B S et al. Arch Pharm Res 29:302-309, 2006), autoimmune thyroiditis (Damotte I D et al. Fur Cytokine Netw 14:52-59, 2003), primary biliary liver cirrhosis (Ballet E et al.

J. Autoimmun 22:153-158, 2004), and Guillain-Barre syndrome (Yuki N et al. Proc Natl Acad Sci USA 101:11404-11409, 2004).

The inventors of this invention have shown previously that oral administration of anti-LPS antibodies effectively suppressed the development of arthritis in this arthritis model (JP-A2006-151914). This evidence suggests strongly that the removal of endotoxin from the gastrointestinal tract is one of the best strategies for the treatment of autoimmune diseases.

There are a variety of difficulties in mass-producing an antibody for medical use, in addition to the high production cost. Antibody, which is a protein, is heat labile, and tends to lose biological activity during processing. Furthermore, an antibody administered by the oral route will be less effective because of its degradation by digestion enzymes in the gastrointestinal tract. Therefore, it is desired to develop a new and effective endotoxin antagonist which is heat-stable, easy to mass-produce at a low cost and safe for humans.

The contamination of endotoxin in injectable products must be removed completely, since even a minor contaminant of endotoxin induces adverse effects such as fever in patients. In order to remove endotoxin from medical products, several adsorbents specific to endotoxin have been used. Synthetic fibers, fabrics and particles covalently bound by a substance that has a high binding affinity to endotoxin, have been used. By contacting these adsorbents with an objective solution, endotoxin contaminated in the solution can be removed effectively. Several endotoxin-adsorbents, such as Affi-Prep Polymixin (BioRad, USA) and Toraymyxin (Toray Medicals, Japan), JP-A 11-335396 and JP-A 2002-263486, are currently used to remove endotoxin contaminated in injectable products and others.

SUMMARY OF THE INVENTION

The present invention provides a non-digestible and non-absorbable endotoxin-adsorbent, used for oral administration, comprising particles in which not more than 1% have a diameter of not more than 5 μm, and more than 90% of the particles have a diameter of not more than 50 μm, based on a volume-based size distribution analysis.

Furthermore, this invention also provides a formulation of the endotoxin-adsorbent or an agent for preventing and treating autoimmune diseases, a method for prevention and treatment of patients with autoimmune diseases by administering the endotoxin-adsorbent, and methods for the manufacture of endotoxin-adsorbents used for the prevention and treatment of autoimmune diseases.

DETAILED DESCRIPTION OF THE INVENTION

Endotoxin-adsorbent used for the treatment of patients with autoimmune diseases requires the following criteria: 1) a high endotoxin-binding capacity, 2) suitable physiological features for oral administration usage and 3) a high margin of safety without any adverse effects. The number of microorganisms residing in the human gastrointestinal tract is believed to be approximately 100 trillion, and the number of endotoxin-containing microorganisms among these bacteria is also massive. Therefore, in order to remove large portions of endotoxin in the gastrointestinal tract, the endotoxin-adsorbent must have a high binding capacity of endotoxin.

In order to satisfy these requirements, new endotoxinadsorbents, which have a high endotoxin-binding capacity, high margin of safety, and suitable physical features for oral administration use, are provided in this invention.

The toxic core of an endotoxin molecule is located in the Lipid A region. This invention consists of a Lipid A-binding substance and insoluble carrier particles in order to adsorb and eliminate large amounts of endotoxin from the gastrointestinal tract into feces by oral administration, for preventing and treating autoimmune diseases such as rheumatoid arthritis.

The endotoxin-adsorbent suitable for the usage of above purposes is as follows:
1. Endotoxin binding capacity of the particles is not less than $10 \times 10^6$ endotoxin units (EU) per 1 g of dry particles in an in-vitro test tube assay.
2. Endotoxin binding capacity of the particles is not less than $50 \times 10^6$ endotoxin units (EU) per 1 g of dry particles in an in-vitro test tube assay.
3. Endotoxin binding capacity of the particles is not less than $100 \times 10^6$ endotoxin units (EU) per 1 g of dry particles in an in-vitro test tube assay.
4. The endotoxin-adsorbent consists of an endotoxin-binding substance and carrier particles.
5. The endotoxin-adsorbent consists of a Lipid A binding substance, that is capable of binding endotoxin.
6. The endotoxin-adsorbent, which is a Lipid A binding substance, is polymixin B.
7. The endotoxin-adsorbent consists of a Lipid A binding substance, polymixin B, and carrier particles which are a weakly acidic cation exchange resin with a carboxy residue.
8. The methods for prevention and treatment of autoimmune diseases by administrating pharmacologically effective doses of an endotoxin-adsorbent to patients by the oral route. Several materials such as polymixin B or a peptide antibiotic, and endotoxin-binding peptides (JP-A 11-335396, JP-A 2002-263486, JP-A 2002-311029, JP-A 2004-292357 and JP-A 2002-512140) have been known as Lipid A-binding substances. All these materials can be used for the purpose of this invention.

The carrier of the endotoxin-binding substance is desired to be small particles or powder suitable and convenient for oral administration usage. A variety of polysaccharides and their derivatives, such as cellulose, agarose, mannan, glucan, and chitin, or a variety of synthetic polymers, such as polyacrylate, polystyrene, polypropylene, polyamide, and polyvinyl, can be used as the carrier of an endotoxin-binding substance.

There is no definite method required to conjugate the Lipid A binding substance to the carrier particles. Cross-linkers which have been widely used for immobilizing enzymes onto the solid surfaces, like water-soluble carbodiimides such as ECDI, hexamethylene diisocyanate, propyleneglycol di-glycidylether, which contains 2 epoxy residues, and epichlorohydrin, can be used.

The features of Lipid A-binding substance-carrier complexes are desired to be non-toxic, non-absorbable, and non-digestible by digestion enzymes and by microorganisms and resistant to other intestinal components such as gastric acid. "Non-digestible" means resistant to both digestion enzymes of animals and enzymes produced by microorganisms.

The microorganisms residing in the gastrointestinal tract possess enzymes which are capable of digesting cellulose and other substances that are resistant to the digestion enzymes of animals (Kopecny J et al. Detection of cellulolytic bacteria from the human colon. Folia Microbiol (Praha) 49:175-7, 2004, Nakajima N et al. Dietary-fiber-degrading enzymes from a human intestinal *Clostridium* and their application to oligosaccharide production from nonstarchy polysaccharide using immobilized cells. Appl Microbiol Biotechnol 59: 182-9, 2002). Therefore, in this invention, the materials used as a carrier of the LPS-binding substance should be restricted to materials, which are resistant to bacterial digestion, and usage of polysaccharides such as cellulose, agarose, mannan, glucan, and chitin as a carrier of an endotoxin-binding substance should be excluded.

Compared to naturally occurring polymers, synthetic polymers are generally resistant to digestion enzymes secreted into the gastrointestinal tract of animals and even to various bacterial enzymes. Therefore, it is desired to choose a synthetic polymer as a carrier of the lipid A-binding substance. In fact, synthetic polymers such as polystyrene sulfonate calcium and anion exchange resin are widely used as a potassium adsorbent and as a cholesterol adsorbent for treatment of patients with high potassium and high cholesterols, respectively.

The particle size of the endotoxin-adsorbent is an important factor that should be considered, since it has been known that small size particles, such as yeast, of less than 5 μm in diameter, are phagocytized by M cells, which reside on the surface of Peyer's patches scattered along small and large bowel regions (Gerbert A. et al. M cells in Peyer's patches of the intestine. Int Rev Cytol. 167:91-159, 1996). Therefore, a particle size of endotoxin-adsorbent of not more than 5 μm in a diameter is excluded according to the specification of polystyrene sulfonate calcium defined in Japanese Pharmacopoeia.

The molecular weight of endotoxin is more than 10,000 daltons, and assumed to bind mainly on the surfaces of endotoxin-adsorbent particles rather than the inside of the particles. Therefore, if the particle size is smaller, the endotoxin-binding capacity is larger due to the larger surface area per unit weight of particles. This evidence is shown in EXAMPLE 12.

There are two classes of fine grinding techniques, dry and wet methods. The impact method, screen method, grind method and others are known as dry methods, whereas the catalyst-stirring method is an example of a typical wet method. There are several other methods, but there is no limitation in the methods for grinding the particles of the endotoxin-adsorbent, and any of these methods can be used for preparing fine powder or small particles of the endotoxin-adsorbent.

The particle size of the endotoxin-adsorbent was determined based on the particle size distribution method. The particle distribution analysis was performed according to "The method for determining particle size distribution. Method 1: Microscopic method" in the second supplement of the general test procedures, section 65, Japanese Pharmacopoeia, 13$^{th}$ Issue. The 50% particle size (μm) was explained as the diameter of particles of the corresponding values of the accumulative volume of particles is 50%.

The LPS binding capacity of the endotoxin-adsorbent in a test tube was determined according to the method described in "endotoxin test procedures" in Japanese Pharmacopoeia, in addition to a simple assay method of LPS by measuring OD values, which was developed during this invention. The experimental procedures and results are shown in EXAMPLE 10 and 11 in detail.

The therapeutic effect of the endotoxin-adsorbent on autoimmune diseases can be determined in the mouse arthritis model as described in our previous invention, JP-A 2006-151914. Briefly, arthritis can be induced in 100% of mice by IP injection of enough amounts of anti-type II collagen monoclonal antibody cocktail (Chondrex Inc., Redmond, Wash., USA) within 3 days (Terato K et al. Induction of arthritis with monoclonal antibodies to collagen. J. Immunol. 148:2103-2108, 1992). By reducing the dose of the monoclonal antibody cocktail to 2 mg, all mice remained normal without developing arthritis. However, oral administration of 3 mg of LPS on 3 consecutive days from day 0, day 1, day 2 and day 3 into these mice induced clinically apparent arthritis, which reached the peak on day 6-7. Furthermore, one group of mice was co-administered with indomethasin and ovoinhibitor, a protease-inhibitor purified from egg white. The combination of indomethasin and ovoinhibitor was used to increase the mucosal permeability of gastro-intestinal mucosa. In these mice, the effect of LPS was more significant, and more severe arthritis was induced by oral administration of a same dose of LPS. Using this arthritis model induced by a combination of monoclonal antibody and LPS, the therapeutic effect of the endotoxin-adsorbent can be determined. The benefit of this model is multifold: time of experimentation is short compared with an authentic collagen-induced arthritis model, the standard deviation of severity of arthritis among individual mice is much less, and the effect of the LPS-adsorbent is clearly determined.

Since the endotoxin-adsorbent is used as a therapeutic agent for human patients by oral administration, various formulas, which are currently employed in medicines used by oral administration, can be applied: for example, a powdered or suspended powdered form, capsule, tablet and solution. These formulas can be provided using authentic methods by mixing the endotoxin-adsorbent with various vehicles and additives within a range that is acceptable with respect to pharmaceutical guidelines.

The endotoxin-adsorbent can be administered orally at 10 mg-10 g per adult by a single or three administrations per day.

EXAMPLES

The individual examples of this invention are described in detail in the following sections, but the invention is not to be considered limited to these examples as described below.

Example 1

Epoxyacryl Resin-Polymixin B Conjugate (RPMB)

Polymixin B sulfate (3 million units, Maruko Pharmaceuticals) was dissolved in 200 mL of 0.1M NaCl, and then the pH was adjusted to 8 by adding NaOH. Four grams of a polyacryl resin with an epoxy residue (Amberzyme, Rohm and Haas, USA) was added to the solution and stirred using a blade propeller for 72 hours. The resin was washed with 1000 mL of distilled water on a membrane filter with a 5 μm pore size, and suspended in 50 mL of 1M glycine solution, pH 8.0, adjusted by NaOH. After incubation overnight, the resin was washed with 2 liters of distilled water on a filter, and dried in a desiccator. The yield of polymixin B-conjugated resin (this is called as RPMB) was 3.9 g.

Example 2

Epoxyacryl Resin-Polymixin B Conjugate (RPMB-1)

Polymixin B sulfate (3 million units, Maruko Pharmaceuticals) was dissolved in 200 mL of 0.1M NaCl, and pH adjusted to 8 by adding NaOH. Four grams of a polyacryl resin with an epoxy residue (Amberzyme, Rohm and Haas, USA) was transferred into a mortar, and ground with a pestle by adding polymixin B sulfate solution drop-wise. The Polymixin B and epoxyacryl resin were stirred for 72 hours using a magnetic stirring bar. The resin was washed with 1 liter of distilled water on a membrane filter with a 5 μm pore size, then suspended in 50 mL of 1M glycine solution, pH 8.0, adjusted with NaOH. After incubation overnight, the resin was washed with 2 liters of distilled water on a filter and dried in a desiccator. The yield of polymixin B-conjugated resin (this is called as RPMB-1) was 3.2 g.

Example 3

Epoxyacryl Resin-Polymixin B Conjugate (RPBM-2)

One gram of a polyacryl resin containing an epoxy residue (Amberzyme, Rohm and Haas, USA) was ground with a mortar and pestle. The powdered resin was suspended in 20 mL of distilled water, reacted with 0.6 g of epichlorohydrin and 0.3 mL of 50% NaOH for 2 hours. The resin was washed with 100 mL of distilled water on a membrane filter with a 5 µm pore size, and then mixed with in 5 mL of 1M phosphate buffer, pH 10.0, containing 3 million units of polymixin B, and stirred at 40° C. for 16 hours. After the reaction, the resin suspension was added by 50 mL of 1M glycine solution, pH 8.0, adjusted with NaOH, and kept overnight. The resin was washed with 2 liters of distilled water on a filter and dried in a desiccator. The yield of polymixin B-conjugated resin (this is called RPMB-2) was 0.5 g.

Example 4

Weakly Acidic Cation-Exchange Resin-Polymixin B Conjugate

Four grams of a weakly acidic cation-exchange resin with carboxyl residues (Dowex MAC-3), was suspended in 50 mL of 0.1M MOPS (3-morpholinopropanesulfonic acid) solution, pH 7.5, and then reacted with 1 g of 1-Ethyl-3-(3-dimethylaminopropyl) carbodiimide hydrochloride (Sigma, USA), a coupling agent, at 4° C. for 2 hours with stirring. The activated resin was collected on a membrane filter with a 5 µm pore size and washed with 200 mL of distilled water. The washed activated resin was then suspended in 50 mL of 0.1M MOPS, pH 7.5, and then mixed with 3 million units of polymixin B dissolved in 10 mL of 0.1M MOPS solution, pH 7.5, and reacted at 4° C. for 16 hours with stirring. The resin was collected on a membrane filter with a 5 µm pore size and then suspended in 50 mL of 1M glycine solution, pH 8.0, adjusted with NaOH, and kept at 4° C. overnight, washed with 2 liters of distilled water and then dried in a desiccator. The yield of polymixin-conjugated weakly acidic cation exchange resin (This preparation is called 4/300) was 3.8 g.

Example 5

Weakly Acidic Cation-Exchange Resin-Polymixin B Conjugate (1/300)

Using the same resin (Dowex MAC-3) and same procedures shown in the Example 4, except for reducing the amount of resin from 4 to 1 g, 0.9 g of polymixin B-conjugated weakly acidic cation exchange resin was obtained. This preparation is called 1/300.

Example 6

Weakly Acidic Cation-Exchange Resin-Polymixin B Conjugate (4M/300)

Four grams of weakly acidic cation-exchange resin with carboxyl residues (Dowex MAC-3), was ground with a mortar and pestle, and suspended in 50 mL of 0.1M MOPS, pH 7.5. The resin was reacted with 1 g of 1-Ethyl-3-(3-dimethylaminopropyl) carbodiimide hydrochloride (Sigma, USA), a coupling agent, at 4° C. for 2 hours with stirring. The activated resin was collected on a membrane filter with a 5 µm pore size and washed with 200 mL of distilled water. The resin was suspended in 50 mL of 0.1M MOPS, pH 7.5, and then added to 10 mL 0.1M MOPS, pH 7.5, containing 3 million units of polymixin B. Polymixin B and the resin were reacted at 4° C. for 16 hours with stirring. The resin was collected on a membrane filter with a 5 µm pore size and then suspended in 50 mL of 1M glycine solution, pH 8.0, adjusted with NaOH, and kept overnight, washed with 2 liters of distilled water, and then dried in a desiccator. The yield of polymixin B-conjugated weakly acidic cation exchange resin was 3.1 g. This preparation is called 4M/300.

Example 7

Weakly Acidic Cation-Exchange Resin-Polymixin B Conjugate (1M/300)

Using the same resin and same procedures as described in Example 6, except for reducing the amount of resin from 4 to 1 g, 0.52 g of polymixin B-conjugated weakly acidic cation exchange resin was obtained. This preparation is called 1M/300.

Example 8

Large Scale Grinding of Resin

Dowex Mac-3 resin (diameter: 300-1200 mm), 3300 liters, was ground using a Dalton NeaMill, NEA-48 type. The yield of powdered Mac-3 was 1400 kg and the average particle size was 30 µm, ranging from 10 to 50 µm.

Example 9

Measurement of Particle Size Distribution

The particle size distribution was measured according to "Measurement of Particle Size Distribution. Method 1: Microscopic method" in the second supplement of the general test procedures, Section 65, Japanese Pharmacopoeia, 13th Issue. The microscope and camera used for this experiment was Nikon ECLIPSE E600 and Victor KY-F55B, respectively. The collected data was analyzed using Nano Hunter NS2K-Pro. The result of analysis of 1006 particles of RPME prepared in Example 1 by this method is shown in Table 1. The 50% particle size of RPMB was 213 µm, and the content of small particles not more than 5 µm in a diameter was 0%.

TABLE 1

Distribution of Particles Size of RPMB*

| Distribution of Particle Size | Diameter |
| --- | --- |
| 10% Diameter | 160 (µm) |
| 50% Diameter | 213 (µm) |
| 90% Diameter | 266 (µm) |
| Average Diameter | 197 (µm) |

*Total 1006 particles were analyzed.

Example 10

Endotoxin Adsorption and Elimination Capacity (1)

Endotoxin was assayed by an end point colorimetric assay method using Endospecy-ES24S kit (Seikagaku Kogyo, Japan). Lipopolysaccharide (LPS) from *E. coli* O-111 (Sigma L4130) was dissolved in pyrogen-free water at 5 µg/mL. One mL of this LPS solution was mixed with 50 µg and 100 µg of RPMB-1, and 100 µg of polymixin B-unconjugated resin (control) and incubated at 37° C. with stirring. Endotoxin levels were determined in the supernatant before, 10 and 20 minutes after adding the resins. As shown in Table 2, LPS was specifically adsorbed by RPMB-1.

TABLE 2

Endotoxin removal activity of RPMB determined by limulus assay

| Resin | Amount (µg) | LPS Activity (EU/mL) Remaining | | |
|---|---|---|---|---|
| | | Before | 10 mm | 20 mm |
| RPMB-1 | 50 | 5632 | 2403 | 1207 |
| RPMB-1 | 100 | 5526 | 1004 | 170 |
| Control Resin | 100 | 5711 | 4605 | 4988 |

Example 11

Endotoxin Adsorption and Elimination Capacity (2)

The endotoxin-binding capacity of polymixin B conjugates was also studied. LPS (Sigma L4130) was dissolved in pyrogen-free water at 0.2 mg/mL, and 4 mL of this solution was added to a test tube containing 20.6 mg of RPMB-1, and incubated at 37° C. with stirring. The supernatant was collected every 30 minutes by centrifugation and the OD values at 210 nm was determined. The OD210 value was dropped from 1 to 0.6 within the first 30 minutes of incubation and remained unchanged afterwards. By adding 20.5 mg of fresh RPM-1 into the supernatant, the OD value was slightly reduced from 0.6 to 0.4. Therefore, it was assumed that 20.6 mg of LPS adsorbent added in the first test tube was saturated with LPS. Accordingly, an LPS adsorption capacity of RPMB-1 was calculated based on the OD value changes of LPS solution. Since the LPS preparation used in this experiment was not pure and contaminated by DNA and proteins, it was assumed that the final OD value of 0.4 reflected the OD value of such contaminants. Based on this assumption, it was calculated that 1 g of RPMB is capable of binding approximately 25.9 mg of LPS (Sigma L4130) using the following formula:

$$(0.8 \text{ mg} \times 0.4/0.6)/0.0206 = 25.9 \text{ mg}$$

Since the endotoxin unit of this LPS preparation is $1.1 \times 10^6$ EU/mg, it was calculated that 1 g of RPMB-1 is capable of binding $29 \times 10^6$ EU of endotoxin.

Example 12

Effect of Particle Size on Endotoxin-Binding Capacity

Polymixin B-conjugated resins prepared in Examples 1-7 were analyzed for their particle size distribution by the method described in Example 9 and assayed for the endotoxin-binding capacity by the method described in Example 11 to study the relationship between particle size and LPS-binding capacity. AffiPrep poplymixin B (BioRad, USA) was used as a reference.

The endotoxin-binding capacity of individual batches of endotoxin-adsorbents prepared by conjugating with 3 million units of polymixin B was compared and expressed as endotoxin units (EU) per gram weight of resin as well as LPS weight per gram resin. The weight of LPS was obtained by converting the EU values based on the EU value per mg of LPS preparation (Sigma L4130, LPS preparation from *E. coli* O-111, B4, by trichloroacetic acid extraction) used for this experiment.

In spite of using the same amount of 3 million units of polymixin B to make conjugates as described in Example 1-7, it was apparent that the endotoxin-binding capacity of polymixin B-conjugated resin is higher if the 50% particle size is smaller as shown in Table 3.

TABLE 3

Relationship between particle sizes and endotoxin-binding capacity

| Polymixin B-Conjugated Resins | 50% Particle Size (µm) | Endotoxin-Binding Capacity (EU/g) | Endotoxin-Binding capacity (LP5 mg/g*) |
|---|---|---|---|
| AffiPrep Polymixin B (Reference) | 61 | $14 \times 10^6$ | 12 (mg) |
| RPMB | 213 | $20 \times 10^6$ | 17.5 (mg) |
| RPMB-1 | 32 | $29 \times 10^6$ | 26.5 (mg) |
| RPMB-2 | 32 | $120 \times 10^6$ | 105 (mg) |
| 4/300 | 400 | $7.2 \times 10^6$ | 6.3 (mg) |
| 1/300 | 400 | $7.7 \times 10^6$ | 6.7 (mg) |
| 4M/300 | 26 | $29.5 \times 10^6$ | 30 (mg) |
| 1M/300 | 29 | $136.3 \times 10^6$ | 120 (mg) |

*Converted to dry weight of LPS

Example 13

Evaluation of Endotoxin-Adsorbent in Autoantibody Mediated, LPS-Induced Arthritis Model DBA/1JNCrj mice (Japan Charles River) were divided into 5 groups (G1-G5, 5 mice per group). In order to increase the mucosal permeability, all mice received 40 µg of indomethasin (Sigma) and 2 mg of ovomucoid (Sigma) for 5 consecutive days from day −6 to −2 by the oral route. On day 0, all mice received an IV injection of 0.2 mL of arthritogenic monoclonal antibody cocktail (10 mg/mL). Endotoxin derived from *E. coli* O-111 (Phenol extracted LPS, Sigma) was dissolved in PBS at 7.5 mg/mL, and 0.2 mL of this solution was administered into G1-G4 mice by the oral route for 3 consecutive days from day 0 to 2. Endotoxin-adsorbent, RPMB-1, was suspended in distilled water at 100 mg/mL, and deaerated by a vacuum pump to keep the particles in uniform suspension by preventing the aggregation of the particles. The RPMB-1 suspension was administered to mice at doses of 0.125 mL (G2), 0.25 mL (G3) and 0.5 mL (G4) twice a day for 4 consecutive days from day 0 to 3 after LPS administration. G1 received 0.25 mL of water alone. Mice in G5, a positive control of arthritis, received IP injection of 0.1 mL of LPS solution (0.5 mg/mL in PBS) on day 3.

All mice were observed for the development of arthritis every day from day 0 to 14. Severity of arthritis was scored by 5 grades, 0: normal without any swelling, 1: clinically apparent swelling of one digit, 2: moderate redness and swelling of more than 2 digits or moderate redness and swelling of the entire paw, 3: severe redness and swelling of the entire paws, and 4: maximum inflamed limb with involvement of multiple joints. The sum of the arthritis score (maximum 16 per mouse) of individual animals was calculated. The effect of the endotoxin-adsorbent was calculated based on the average score of 5 mice using the following equation:

Suppression of arthritis(%)=(1−Average score of test group/Average score of control group)×100

Since the arthritis scores reached a maximum on day 7, the effect of the endotoxin-adsorbent was calculated using the scores on day 7. The suppression of arthritis by RPMB prepared in EXAMPLE 2 at 25 mg, 50 mg and 100 mg per mouse by oral administration is shown in Table 3. None of the five mice which received 100 mg of RPMB-1 developed arthritis, whereas 2 out of 5 mice which received 50 mg of RPMB-1 developed mild arthritis (average score: 2), and 4 out of 5 mice which received 25 mg of RPMB-1 developed moderate arthritis (average score: 9) (Table 3, experiment 1), indicating a dose response effectiveness of RPMB-1.

Similarly, RPMB-2, 1M/300 and 4M/300, which have higher binding capacities of LPS then RPMB-1, were also tested for their effect on arthritis at a dose of 10 mg per mouse. All three preparations were equally effective and suppressed the development of arthritis almost completely (Table 3, experiment 2)

TABLE 3

Suppression of arthritis by polymixin B conjugated resins

| Experiment No | Polymixin B-Conjugated Resin | Dose (mg/mouse) | Incidence of Arthritis | Severity of Arthritis (score) |
|---|---|---|---|---|
| 1 | Control Resin | 50 | 5/5 | 12 ± 1.6 |
|   | RPMB-1 | 25 | 4/5 | 6.4 ± 1.8 |
|   | RPMB-1 | 50 | 2/5 | 2 ± 2.8 |
|   | RPMB-1 | 100 | 0/5 | 0 ± 0 |
| 2 | Control Resin | 10 | 5/5 | 12.6 ± 1.1 |
|   | RPMB-2 | 10 | 0/5 | 0 ± 0 |
|   | 4M/300 | 10 | 1/5 | 0.8 ± 1.8 |
|   | 1M/300 | 10 | 0/5 | 0 ± 0 |

Example 14

Tablet

The tablets were prepared by mixing 15 g of 1M/300, which was prepared in EXAMPLE 7, 2.5 g of lactose, 2.4 g of corn starch, and 0.1 g of magnesium stearate. These four components were mixed well and compressed by a single punch tableting machine to make tablets containing 200 mg of 1M/300 per a tablet.

Example 15

Capsule

RPMB-2 powder shown in EXAMPLE 3 was dispensed into hard capsules at 150 mg per a capsule.

What is claimed is:

1. A method of treating rheumatoid arthritis in a patient having rheumatoid arthritis comprising the step of orally administering to the patient a pharmacologically effective amount of an endotoxin-adsorbent comprising a Lipid A-binding molecule having an endotoxin-binding activity and particles carrying the Lipid A-binding molecule, wherein the Lipid A-binding molecule is polymixin B, and the particles carrying the Lipid A-binding molecule comprise a synthetic polymer having an epoxy residue, and wherein the particles comprise indigestible particles in which no more than 1% of the particles are 5 µm or less in diameter and more than 90% of the particles are 50 µm or less in diameter, based on volume-based distribution analysis.

2. The method of claim 1, wherein the particles carrying the endotoxin-binding active group comprises a polyacryl resin having an epoxy residue.

3. The method of claim 1, wherein the particles carrying the endotoxin-binding active group comprises a polystyrene resin having epoxy residue.

4. The method of claim 1, wherein the synthetic polymer is selected from the group consisting of polyacrylate, polystyrene, polypropylene, polyamide and polyvinyl.

* * * * *